United States Patent [19]

Frist et al.

[11] Patent Number: 4,573,975
[45] Date of Patent: Mar. 4, 1986

[54] PROTECTIVE SHIELD FOR NEEDLE RECEIVER

[76] Inventors: Brian S. Frist, 65 Cameron Glen Dr., Atlanta, Ga. 30328; Wayne H. Lazarus, 50 Bransford Rd., Atlanta, Ga. 30342

[21] Appl. No.: 688,734

[22] Filed: Jan. 4, 1985

[51] Int. Cl.[4] ............................................. A61M 5/32
[52] U.S. Cl. ................................... 604/192; 604/263
[58] Field of Search .............................. 604/192, 263

[56] References Cited
PUBLICATIONS

Comp Gard TM, Comp Equip. Corp. brochure.

*Primary Examiner*—John D. Yasko
*Attorney, Agent, or Firm*—James B. Middleton

[57] ABSTRACT

A protective shield surrounding a container for a hypodermic needle. The container is an elongate container for a needle, the container having a neck adapted to receive a closure. A protective shield is carried at the neck, the shield being foldable down against the body of the container. There is a cylindrical holder at the end of the closure so that, when the closure is in position, the holder, or closure extension, holds the protective shield in folded position. When the closure is removed, the shield expands out to provide the protective shield on reinsertion of the needle into the container.

8 Claims, 4 Drawing Figures

U.S. Patent     Mar. 4, 1986     4,573,975
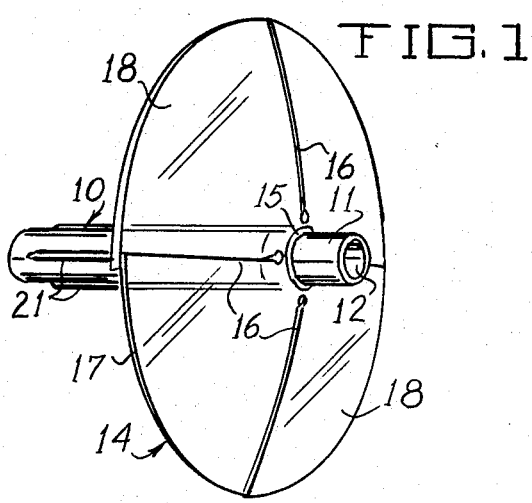
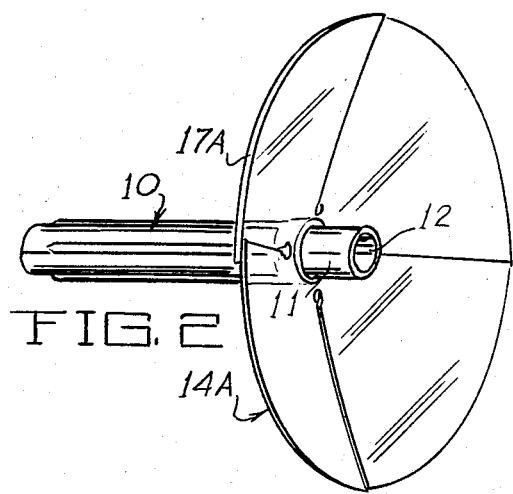
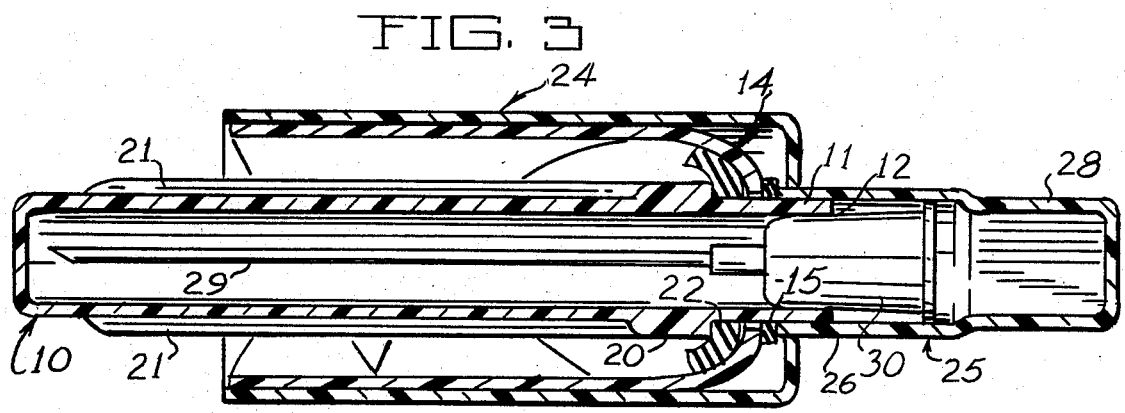
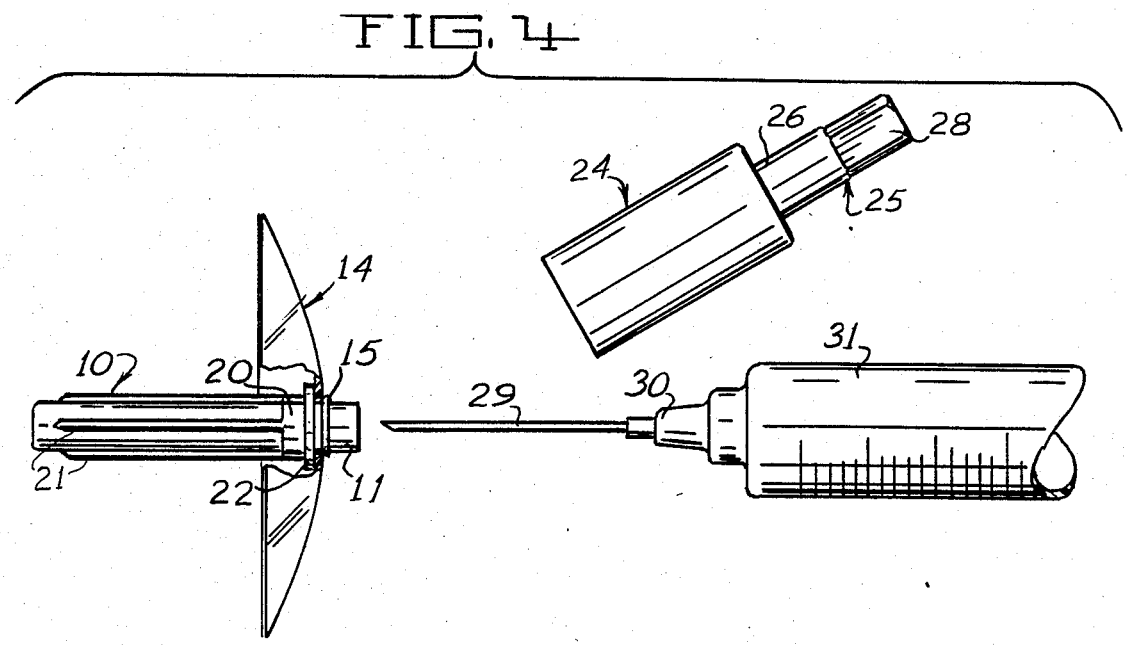

PROTECTIVE SHIELD FOR NEEDLE RECEIVER

INFORMATION DISCLOSURE STATEMENT

A major problem in hospitals and other medical facilities is an appropriate disposition of a hypodermic needle after the needle has been used. It is well known that transmission of hepatitis through accidental injury with hypodermic needles is a major problem.

Some efforts at disposal of used hypodermic needles have included simply depositing the used needle and syringe into a disposal container. Such a technique requires use of a highly specialized container, or the container itself constitutes a hazard in that there is a repository of used needles that can accidentally injure a person. When a container is reasonably well filled with hypodermic needles and syringes, the deposition of an additional syringe may cause one or more of the needles to be displaced and injure the person depositing yet another. In an effort to resolve this problem, there have been needle cutters associated with such boxes so the needle is cut from the syringe prior to deposition in the box. Such needle cutters, however, have also constituted a hazard in that the cutters become dull, and the large forces involved in attempting to cut a needle may cause injury to the person attempting to cut the needle.

There is therefore a continuing need for a means for disposing of a single hypodermic syringe and needle in a safe manner that will not constitute a hazard.

SUMMARY OF THE INVENTION

This invention relates generally to protective shields, and is more specifically concerned with a hypodermic needle receiving container having a shield supported therefrom, the shield being arranged to protect the hand of the person inserting a needle into the receiver.

The present invention provides a needle receiver that may be the original, sterile container for an unused hypodermic needle, the container having a shield therearound so located that, after the hypodermic needle has been used, the needle can be inserted into the container while the shield surrounds the opening of the container to protect the hand of the person holding the container. In the preferred embodiment of the invention, the hypodermic needle will be packaged in sterile condition within a container, and an expansible shield will be carried by the container. A closure for the container includes both the closure itself and a shield holding means for retaining the protective shield in a folded state. With such an arrangement, the needle container is opened, thereby allowing the protective shield to expand. A person can then hold the container, and the protective shield will cover the person's hand adjacent to the opening in the container to protect the person on reinsertion of the needle into the container.

BRIEF DESCRIPTION OF THE DRAWINGS

These and other features and advantages of the present invention will become apparent from consideration of the following specification when taken in conjunction with the accompanying drawings in which:

FIG. 1 is a perspective view illustrating a needle receiving container having a protective shield carried thereby, the shield being shown in expanded form;

FIG. 2 is a view similar to FIG. 1, and showing a slightly modified form of protective shield;

FIG. 3 is a longitudinal cross-sectional view showing the container of FIG. 1 with a needle therein, and the closure closing the container; and, FIG. 4 is a side elevational view showing the closure exploded from the needle container, and the needle removed from the container through attachment to a syringe.

DETAILED DESCRIPTION OF THE EMBODIMENTS

Referring now more particularly to the drawings, and to those embodiments of the invention here presented by way of illustration, it will be seen in FIG. 1 of the drawings that the needle receiver shown in FIG. 1 comprises generally a cylindrical casing 10 having a forward neck 11 and an axial opening 12. There is a somewhat conically shaped protective shield 14 having a central opening which receives the neck 11 of the container 10, and a retainer 15 prevents inadvertent removal of the shield 14 from the neck 11.

Looking at the shield 14 in more detail, it will be understood that the shield 14 will be made of, probably, plastic sheet material. The configuration of the shield 14 is such that the shield can be stamped from sheet material as a disk, with a plurality of radial slits designated at 16. Due to the presence of the radial slits, it will be understood that the various remaining segments 18 of the disk can be overlapped so the circumference of the outer edge 17 of the shield 14 can be reduced, causing the conical shape. It will also be realized that, when the cut edges overlap, additional protection is provided to prevent a needle from passing through a slit 16.

Looking briefly at FIG. 2 of the drawings, it will be seen that the device is substantially the same as the device shown in FIG. 1. The difference is that the shield, here designated at 14A, has its outer periphery 17A forwardly of the center portion of yield a funnel arrangement. The shield 14A is otherwise the same as the shield 14, and no further description is thought to be necessary.

Turning now to FIG. 3 of the drawings, it will be seen that the container 10 is cylindrical, and includes an annular collar 20 adjacent to the neck 11. The collar 20 is here shown as molded integrally with the container 10, and merging with a plurality of longitudinal ribs 21 which may be used to add strength to the container 10.

The annular collar 20 has a flexible washer 22 thereagainst, the washer 22 being received over the neck 11 to abut the collar 20. The washer 22, then, acts as a backup and stop for the protective shield 14.

As illustrated in FIG. 3, that the shield 14 is folded for convenient storage. This folded condition is maintained by the closure extension 24, the closure extension 24 being a generally cylindrical member carried by the closure itself designated at 25.

The closure 25 comprises a cylindrical portion 26 which is so sized as to be received over the neck 11 of the container 10. The rear portion 28 of the closure 25 may be a non-circular configuration to allow better gripping for removal of the closure.

FIG. 3 also illustrates the retainer 15 to hold the shield 14 in place on the neck 11.

Looking next at FIG. 4 of the drawings, it should be well understood by those skilled in the art that the arrangement shown in FIG. 3 of the drawings comprises the package to be sold when a hypodermic needle is purchased. The needle 29 includes the conventional ferrule and attachment means 30 for attaching the needle to a syringe. Thus, when the needle is to be used, the container 10 will be grasped at the lefthand end thereof as viewed in FIGS. 3 and 4, and the closure 25 will be removed, thereby also removing the closure extension 24 from around the protective shield 14. Once the closure 25 is removed, the shield 14 will expand as is illustrated in FIG. 4 of the drawings, and the full length of the needle container 10 can be conveniently grasped. At this point, a conventional syringe can be mated with the attaching means 30, and the needle 29 will be fixed to the syringe 31, so the syringe 31 with attached needle 29 is ready for use.

After use of the needle 29, the needle can be rendered safe by replacing the needle 29 into the container 10. It is normally during such replacement that a person can be inured by inadvertently puncturing himself wiith the used needle 29. However, using the arrangement of the present invention, it will be seen that the container 10 will be held in the person's hand, and the protective shield 14 will completely surround the opening 12 of the container 10 so that, if the needle 29 misses the opening 12, the needle will engage the shield 14 rather than the hand of the person holding the container.

Once the needle 29 has been replaced into the container 10, the syringe 31 can be removed and either reused or disposed of separately, or the syringe can remain attached to the needle for complete, safe disposal.

With the construction shown and described, it should be understood that the washer 22 may be large enough that the washer 22 will be folded along with the protective shield as is illustrated in FIG. 3. When the closure extension 24 is removed, then, the washer 22 will assist in urging the shield 14 to its open position. The retaining means 15 may be a similar washer, O-ring or the like, but the retaining means 15 must be only sufficient to prevent inadvertent removal of the shield 14 over the neck 11 of the container 10.

As here illustrated, there are four slits 16, dividing the shield 14 into four segments 18. It will be understood that the material of the shield 14 is relatively thin and flexible, and the use of four segments allows relatively easy folding of the shield 14 into the configuration shown in FIG. 3. Nevertheless, it will be understood that additional slits 16 may be used to divide the original disk into a greater number of segments 18 if desired. Also, those skilled in the art will devise other means for folding the shield 14, such as accordion pleating or the like, and the other shapes may be used in lieu of the circular configuration.

It will therefore be understood that the particular embodiments of the invention here presented are by way of illustration only, and are meant to be in no way restrictive; therefore, numerous changes and modifications may be made, and the full use of equivalents resorted to, without departing from the spirit or scope of the invention as defined in the appended claims.

We claim:

1. A protective shield, for a needle receiver comprising a container for a hypodermic needle, said container having an open top for receiving said needle, and a neck portion adjacent to said open top, said protective shield including a piece of sheet material defining a central opening therethrough, said central opening being adapted to receive said neck portion of said container, said piece of sheet material having a periphery, and means for allowing said protective shield to fold whereby said periphery is effectively shortened and said sheet of material assumes a generally conical shape, a washer carried on said container adjacent to said neck for limiting the motion of said protective shield in one direction, and a retainer carried on said neck for holding said protective shield against said washer.

2. A protective shield as claimed in claim 1, said piece of sheet material having a plurality of slits extending radially of said neck of said container for defining a plurality of segments of said piece of sheet material, each segment of said plurality of segments being movable with respect to adjacent segments for allowing said sheet of material to assume a generally conical configuration.

3. A protective shield as claimed in claim 2, said piece of sheet material defining a disk so that said plurality of segments constitute segments of a circle, said slits extending from the circumference of said disk and terminating before said central opening so that said segments can be urged towards said container by allowing said segments to overlap at said slits.

4. In a container for a hypodermic needle, wherein said container includes a generally cylindrical body having a neck defined at one end thereof, and an opening at said one end for receiving a needle, and a closure receivable over said neck for closing said container and retaining said needle within said container, the improvement comprising a protective sheild received over said neck, said protective shield extending outwardly from said neck, said shield being so constructed and arranged that a needle mis-directed towards said opening for receiving a needle will engage said protective shield to prevent injury to a person holding said container, and wherein said protective shield comprises a piece of flexible sheet material having a generally circular configuration, said piece of sheet material defining a central opening for receiving said neck therethrough, a washer on said container for limiting motion of said piece of sheet material in one direction, and a retainer received on said neck for holding said piece of sheet material against said washer.

5. In a container as claimed in claim 4, the improvement wherein said piece of sheet material defines a plurality of slits generally radially thereof, said slits extending from the circumference and extending to a point radially outwardly of said central opening for defining a plurality of segments moveable relative to one another, adjacent edges of said segments being overlapped for shortening said circumference and causing said piece of material to assume a generally conical shape.

6. In a container as claimed in claim 5, the further improvement comprising means for urging said plurality of segments towards said container to place said protective shield in a folded condition.

7. In a container as claimed in claim 6, said means for urging said plurality of segments towards said container comprising a closure extension including a cylindrical body concentric with said closure and extending forwardly therefrom, the arrangement being such that said closure extension holds said protective shield in folded condition.

8. In a container as claimed in claim 7, the improvement wherein said piece of sheet material is sufficiently resilient that said segments tend to spread out when released to provide said protective shield, said washer being elastomeric to assist in urging said plurality of segments outwardly.

* * * * *